United States Patent [19]

Williams et al.

[11] Patent Number: 5,597,995
[45] Date of Patent: Jan. 28, 1997

[54] AUTOMATED MEDICAL PRESCRIPTION FULFILLMENT SYSTEM HAVING WORK STATIONS FOR IMAGING, FILLING, AND CHECKING THE DISPENSED DRUG PRODUCT

[75] Inventors: Jeffrey P. Williams, Dry Prong, La.; Dana Welin, Chandler, Ariz.; Robert Mathews, Brentwood, Tenn.; Alvin Towle, Boyce; Alec Orrick, Pineville, both of La.

[73] Assignee: Automated Prescription Systems, Inc., Pineville, La.

[21] Appl. No.: 555,272

[22] Filed: Nov. 8, 1995

[51] Int. Cl.⁶ ..................................................... G06F 17/00
[52] U.S. Cl. ..................... 235/375; 235/385; 364/478.13; 364/479.01; 358/403
[58] Field of Search ..................................... 235/375, 383, 235/385, 462; 364/478, 479; 358/403

[56] References Cited

U.S. PATENT DOCUMENTS

| | | | |
|---|---|---|---|
| 3,921,196 | 11/1975 | Patterson | 235/61.11 D |
| 4,283,621 | 8/1981 | Pembroke | 235/375 |
| 4,655,026 | 4/1987 | Wigoda | 53/55 |
| 4,780,599 | 10/1988 | Baus | 235/383 |
| 4,785,969 | 11/1988 | McLaughlin | 221/2 |
| 4,847,764 | 7/1989 | Halvorson | 364/413.02 |
| 4,918,604 | 4/1990 | Baum | 364/413.01 |
| 4,952,785 | 8/1990 | Kikuda | 235/432 |
| 5,208,762 | 5/1993 | Charhut et al. | 364/478 |
| 5,227,893 | 7/1993 | Ett | 358/400 |
| 5,337,919 | 8/1994 | Spaulding et al. | 221/2 |
| 5,448,375 | 9/1995 | Cooper et al. | 358/403 |
| 5,511,594 | 4/1996 | Brennan et al. | 141/98 |

*Primary Examiner*—Donald T. Hajec
*Assistant Examiner*—Michael G. Lee
*Attorney, Agent, or Firm*—Ezra Sutton

[57] ABSTRACT

The present invention provides a pharmacy system for automating the medical prescription fulfillment process for a customer. It includes an imaging work station having a host computer for receiving data entry of an original medical prescription for a prescribed drug product and customer information and for producing a prescription transaction data record; and electronic communication device for communicating the prescription transaction data record from the host computer to a series of computers. A filling work station includes dispensing apparatus for counting, dispensing, and packaging of the dispensed drug product into the drug vial for the customer. A checking work station includes a scanner for scanning the bar code label on the drug vial, and a display for displaying the digitized image of the original medical prescription, and for displaying a digitized image of the prescribed drug product to allow a first visual comparison between the digitized image of the prescribed drug product and the dispensed drug product in the drug vial, and a second visual comparison between the digitized image of the original medical prescription and the dispensed drug product in the drug vial before it is given to the customer.

13 Claims, 5 Drawing Sheets

FIG. 4

AUTOMATED MEDICAL PRESCRIPTION FULFILLMENT SYSTEM HAVING WORK STATIONS FOR IMAGING, FILLING, AND CHECKING THE DISPENSED DRUG PRODUCT

FIELD OF THE INVENTION

This invention relates to an integrated retail pharmacy system having hardware and software components that automate the medical prescription fulfillment process in a retail pharmacy setting from entry of the prescription to payment for it. The system includes at least three work stations that provide the functions of imaging, filling, and checking.

BACKGROUND OF THE INVENTION

Presently, prescriptions are generally processed at retail pharmacies without the assistance of significant amounts of automation and are mostly done manually by the pharmacist. Prescription orders at present are commonly entered into computer systems which do a variety of work flow tasks, such as checking patient profiles and printing of prescription labels, as well as doing the order entry or the payment aspect of the prescription filled. Prescriptions are typically filled by hand with just a few persons, being the pharmacist, technician, clerk, and cashier accomplishing all tasks from order entry to payment.

The drawback of the present retail pharmacy system is that most retail pharmacies use little or no dispensing automation equipment, and they do not use computer components for displaying images of the prescription and the drug for quality control, but instead rely on manpower to process the required workload from start to finish of a patient's medical prescription fulfillment.

DESCRIPTION OF THE PRIOR ART

Pharmacy systems of various designs that partially automate the medical prescription fulfillment process have been disclosed in the prior art. For example, U.S. Pat. No. 5,208,762 to Charhut discloses a method and apparatus for dispensing drugs. This system provides a computer terminal where a pharmacist inputs a patient's identification and prescription; a line of machines that automatically fill, label, cap, and sort vials with one or more prescriptions in accordance with a patient's order; and the moving of the patient's prescription with the use of a sorting conveyor to a pick-up station where the pharmacist manually reviews the patient's order. This system is used for mail-order prescription fulfillment or outpatient pickup but cannot be used for a retail pharmacy situation because of the amount and physical size of equipment involved for the prescription fulfillment part.

U.S. Pat. No. 4,847,764 to Halvorson discloses a pharmacy system for dispensing medications in a health-care institution, such as a nursing home, hospital, or medical clinic. The dispensing system includes such hardware as a digital computer with keyboards, printers, and dispenser interfaces. Other dispensing hardware includes electromechanical dispensers having video display units with keyboards. Essentially, the computer and its associated hardware and software log in all of the crucial patient information for fulfilling the terms of a prescription order set forth by a doctor and an electromechanical dispenser unit for dispensing a given medication for a patient's prescription, with computer backup of various file records set up to monitor the total medication system. This system is mainly used in a hospital setting and not in a retail pharmacy store.

U.S. Pat. No. 4,918,604 to Baum discloses a drug-labeling and prescription-filling system for the dispensing of prescription drugs by a mail service pharmacy or by a retail pharmacy. This system contains a main frame computer controlled by a keyboard terminal, and the computer contains a program to organize each prescription received into prescription labels having the depiction of the pill on the label, prescription instructions, and prescription information, such as patient's name, physicians's name, and other vital data the pharmacist needs to fill the drug prescription. Each prescription filled has the computer assign it a bar code number, which is unique for that prescription. The aforementioned system also includes a microcomputer for the pharmacist, having a display screen, a color printer capable of printing color graphics, a disk file containing the graphics of prescription drugs, and a bar code reader wand, which is used to verify the prescription information. This system does not use any pharmaceutical-dispensing equipment or computer image capturing or drug image display checking hardware and its associated software.

The prior art patents do not disclose a pharmacy system and method for medical prescription fulfillment for retail pharmacies. The prior art patents do not teach the use of computer microprocessors for prescription image capture and display checking for prescription quality control. The prior art patents do not teach the use of pharmaceutical-dispenser apparatus that is integrated for use with computers for retail pharmacies.

Accordingly, it is an object of the present invention to provide for a retail store pharmacy system that automates the medical prescription fulfillment process, including at least three essential work stations of imaging, filling, and checking, which operate under computer guidance from a common database, with the primary benefits of increased efficiency and lower overall cost.

Another object of the present invention is to provide for an imaging work station that is designed to capture an electronic image of the doctor's original prescription to the patient and allows the operator at that work station to set certain prescription processing parameters. This significantly reduces paperwork in the fulfillment process through the use of an imaging system, which maintains the accuracy of the original written prescription.

Another object of the present invention is to provide for a filling work station that controls the dispensing equipment, which includes the counting machines and the vertical carousels with movable shelves as well as common static shelves. This dispensing equipment increases the productivity of the pharmacy by providing access to a broad range of products within a minimum amount of processing floor space of a pharmacy.

Another object of the present invention is to provide for a checking station that is used to assist the pharmacist in the final quality-control checking task, such that the display screen shows both the prescription image and the drug product image, which then requires the pharmacist to sign off that the prescription is filled and labeled properly.

A further object of the present invention is to provide for a retail pharmacy system that is unique, efficient, automated, fast, economical, and effective.

A still further object of the present invention is to provide for a retail pharmacy system that is easily operated with a minimum of manpower to operate the system.

SUMMARY OF THE INVENTION

The present invention provides an apparatus for a retail store pharmacy system that automates the medical prescription fulfillment process. The pharmacy system includes at least three interrelated, essential, and necessary work stations which operate under computer guidance from a centralized and common database. These work stations function as imaging, filling, and checking points in the prescription fulfillment process.

The imaging work station is designed to capture an electronic image of the original medical prescription by the use of an image capture microprocessor which holds the captured prescription image in the database for later recall. The imaging work station also allows the operator to set certain prescription processing parameters. The imaging work station includes a host computer for receiving data entry of an original medical prescription for a prescribed drug product and customer information and for producing a prescription transaction data record. The imaging work station also includes a first computer electronically connected to the host computer and having an image scanner for creating a digitized image of the original medical prescription. The imaging work station further includes a first printer for printing a prescription label for applying to a given drug vial for receiving a dispensed drug product; and a second printer for printing a bar code label for applying to a given drug vial; and means for communicating the prescription transaction data record from the host computer to the first computer at the imaging station.

The filling work station is used to control the components of the drug-dispensing units. The drug-dispensing units may include a plurality of counting-machine devices and a plurality of vertical carousels with movable shelves. The filling station also has other types of drug-dispensing units. The filling work station includes a second computer electronically connected to the first computer at the imaging work station and further includes various dispensing apparatus for counting, dispensing, and packaging of a specific dispensed drug product into a given drug vial for the customer, and where the second computer is used for the controlling the various dispensing equipment.

The checking work station is used to assist the pharmacist in the final quality-control check of the medical prescription just filled. At this station, the computer displays both the doctor's original prescription image and an image of the drug product prescribed for a comparison. The checking work station includes a third computer electronically connected to the second computer at the filling work station and further includes a scanner for scanning the bar code label on a given drug vial, and a display for displaying the digitized image of the original medical prescription, and for displaying a digitized image of a specified prescribed drug product. This final quality-control check requires the pharmacist to make a first visual comparison between the digitized image of the prescribed drug product and the dispensed drug product in the specified drug vial, and a second visual comparison between the digitized image of the original medical prescription and the dispensed drug product in the specified drug vial before it is given to the customer. The pharmacist then signs off by the use of an electronic wand over the pharmacist's personal bar code that the prescription is filled properly.

BRIEF DESCRIPTION OF THE DRAWINGS

Further objects, features, and advantages of the present invention will become apparent upon consideration of the detailed description of the presently-preferred embodiments, when taken in conjunction with the accompanying drawings, wherein:

FIG. 4 is a schematic diagram of the filling work station of the pharmacy system of FIG. 1;

DETAILED DESCRIPTION OF THE PREFERRED EMBODIMENT

Overview

Figure 1:
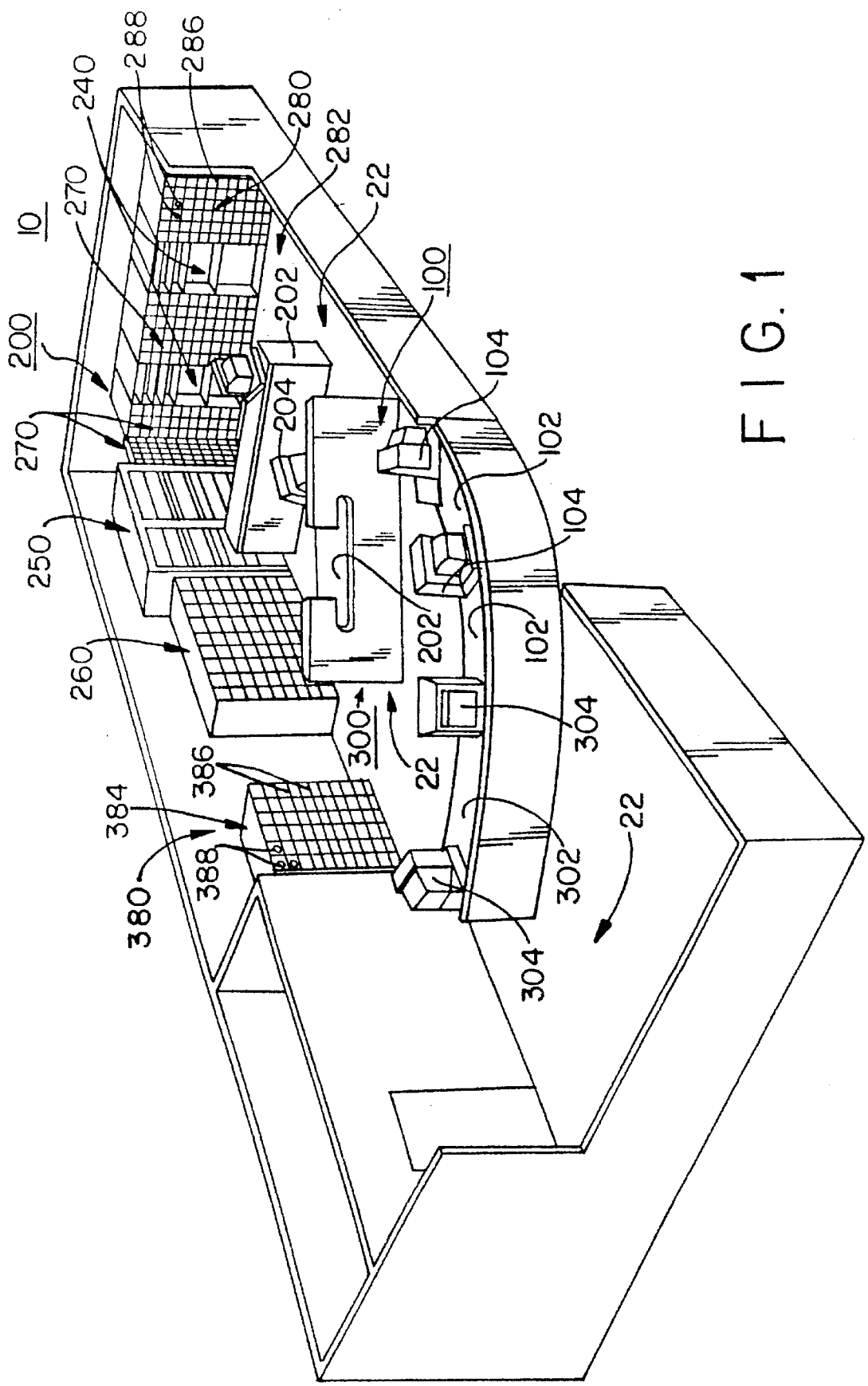
FIG. 1 is a perspective view of the pharmacy system of the present invention showing the imaging, filling, and checking work stations.
Figure 2:
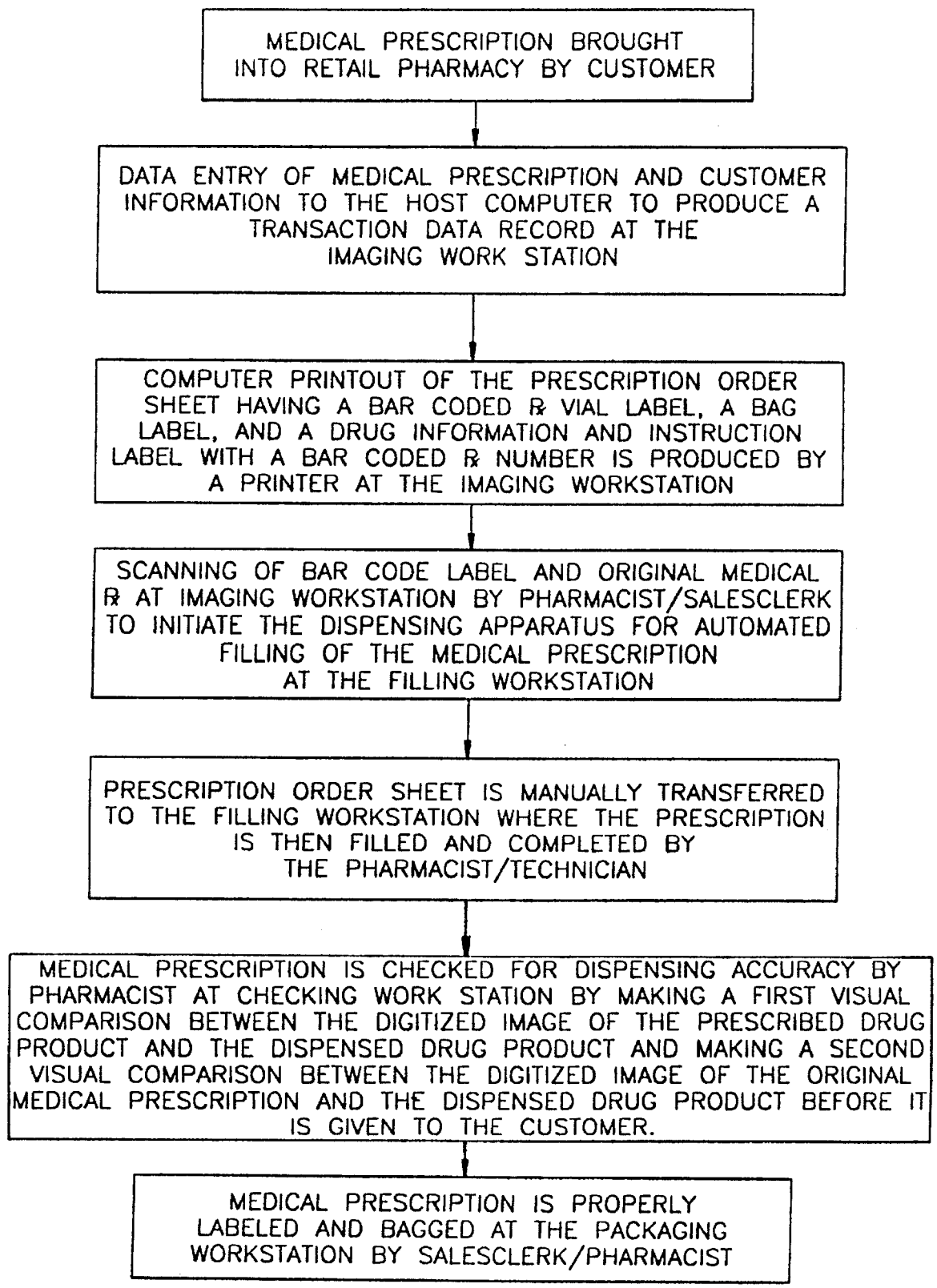
FIG. 2 is a schematic flow diagram of the pharmacy system showing the process of a prescription fulfillment from order entry to payment for the prescription.

The pharmacy system 10 and its component parts of the preferred embodiment of the present invention are represented in detail in FIGS. 1 through 6. The pharmacy system 10 includes hardware components and its associated software for at least three interrelated and essential work stations, including an imaging work station 100, a filling work station 200, and a checking work station 300. These work stations 100, 200, and 300 operate under computer guidance from a centralized database and function as imaging, filling, and checking points in the automated medical prescription fulfillment process of pharmacy system 10, as shown in FIGS. 1 and 2 of the drawings.

Figure 3:
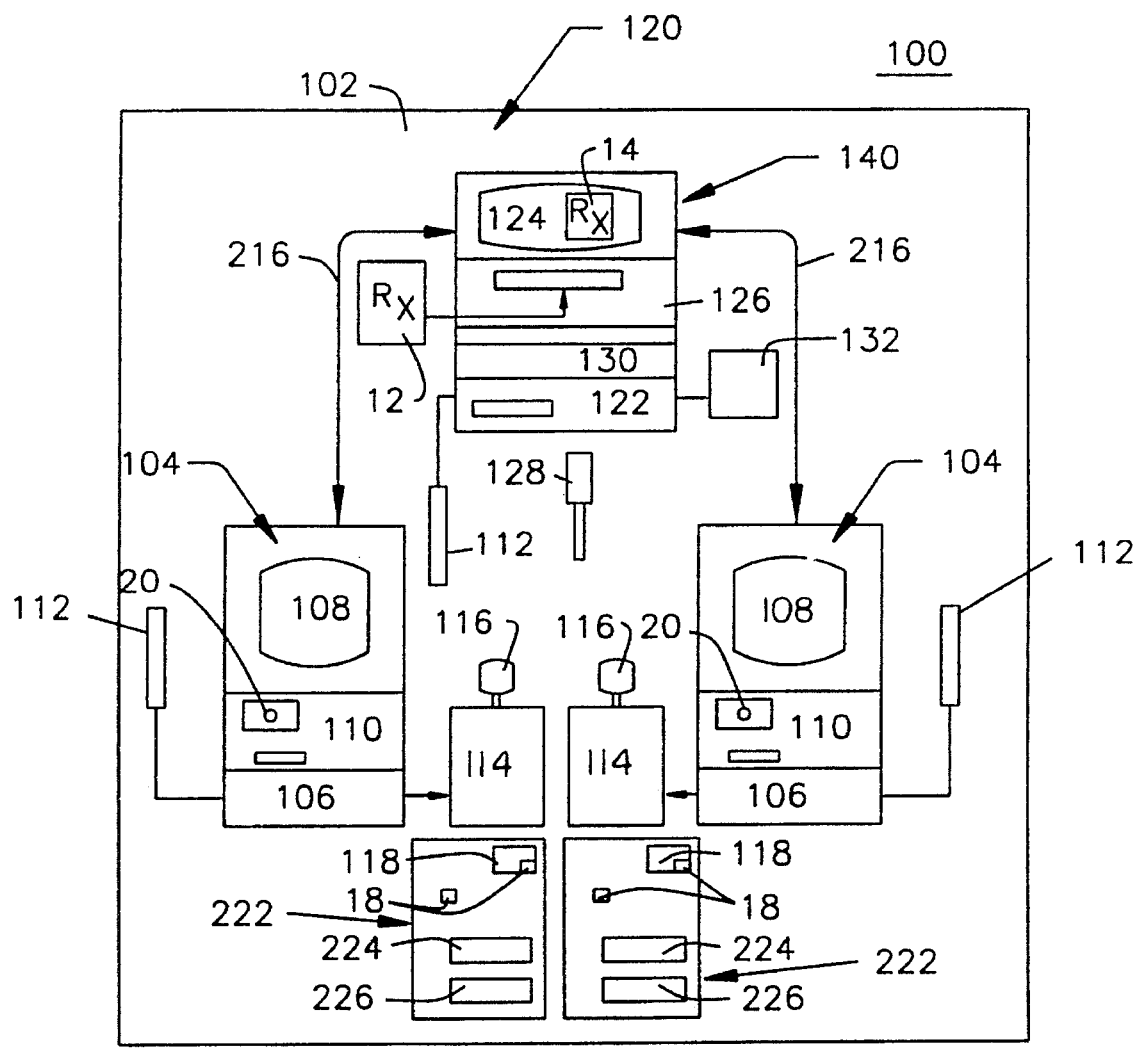
FIG. 3 is a schematic diagram of the imaging work station of the pharmacy system of FIG. 1.
Figure 5:
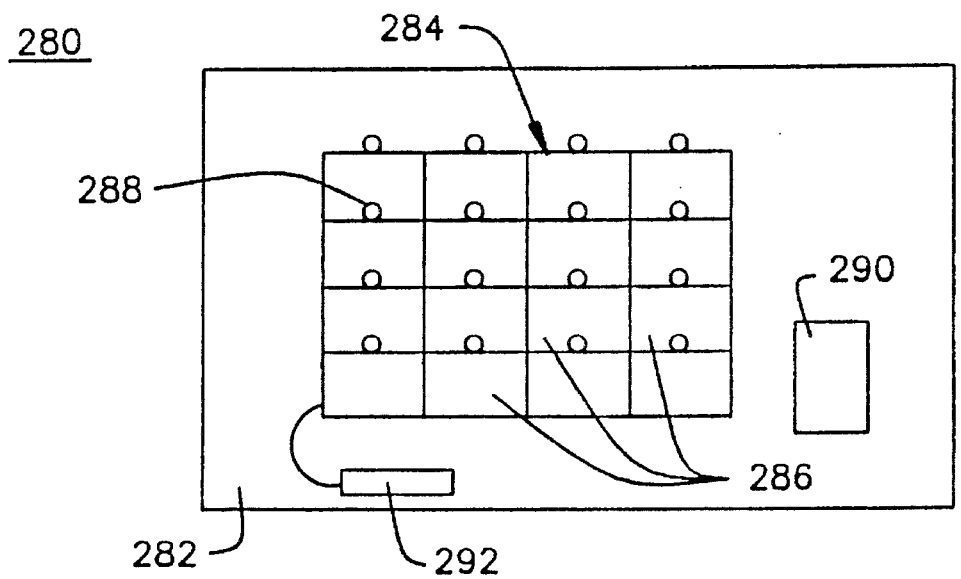
FIG. 5 is a schematic diagram of the packing work station of the pharmacy system of FIG. 1.

The primary function of the imaging work station 100, as depicted in FIG. 3, is to capture an electronic image 14 of the original medical prescription 12 by the use of a host computer 104 having an image capture scanner component 120 which holds the captured prescription image 14 in a database 130 for later recall. The imaging work station 100 also allows the operator to set certain prescription-processing parameters which are stored in a database 110.

Figure 4:
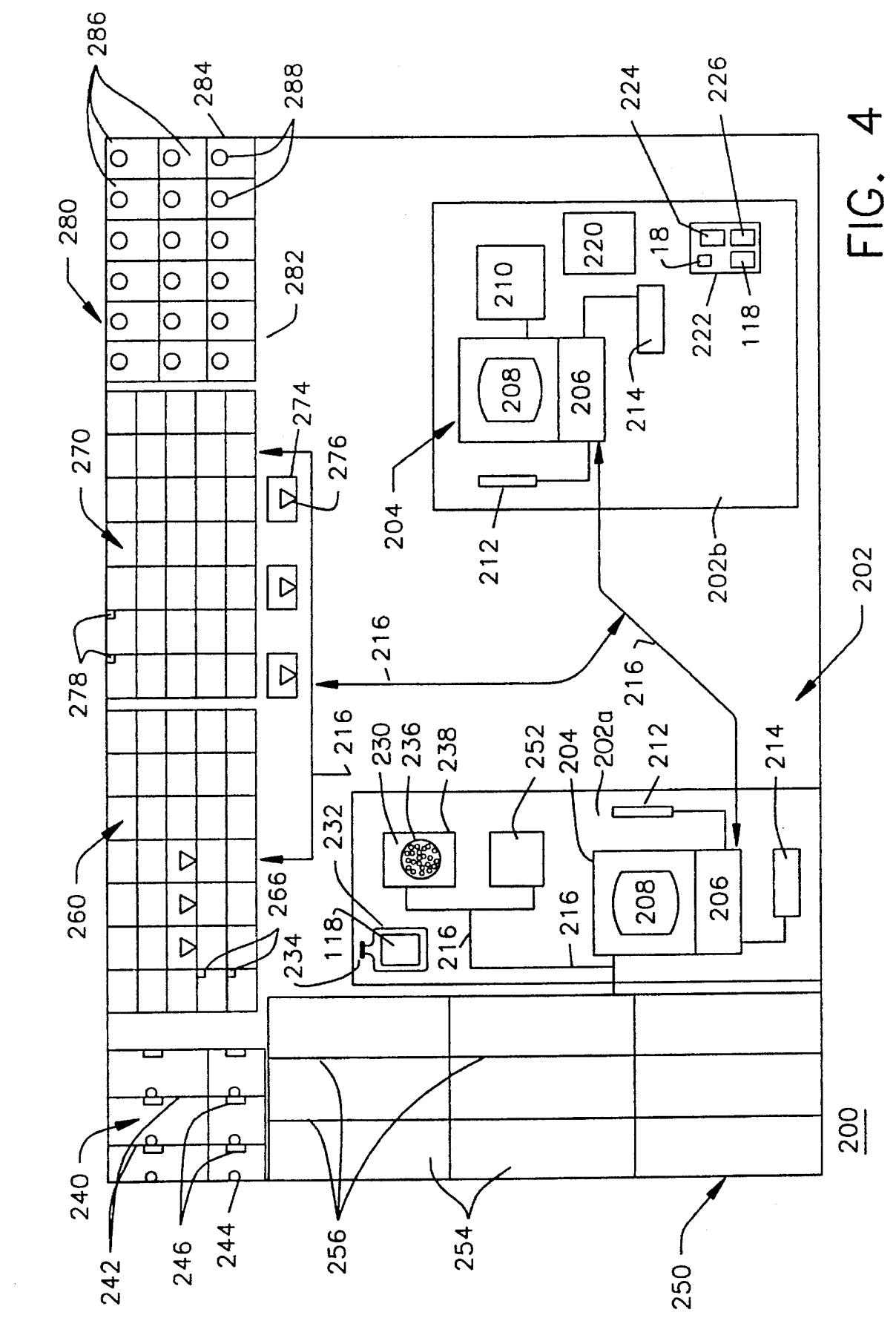

The filling work station 200, as depicted in FIG. 4, is used to control the drug-dispensing units 250, 260, and 270. The drug-dispensing unit 250 includes a plurality of counting-machine devices 252 and a plurality of vertical carousels 254 with movable shelves 256.

Figure 6:
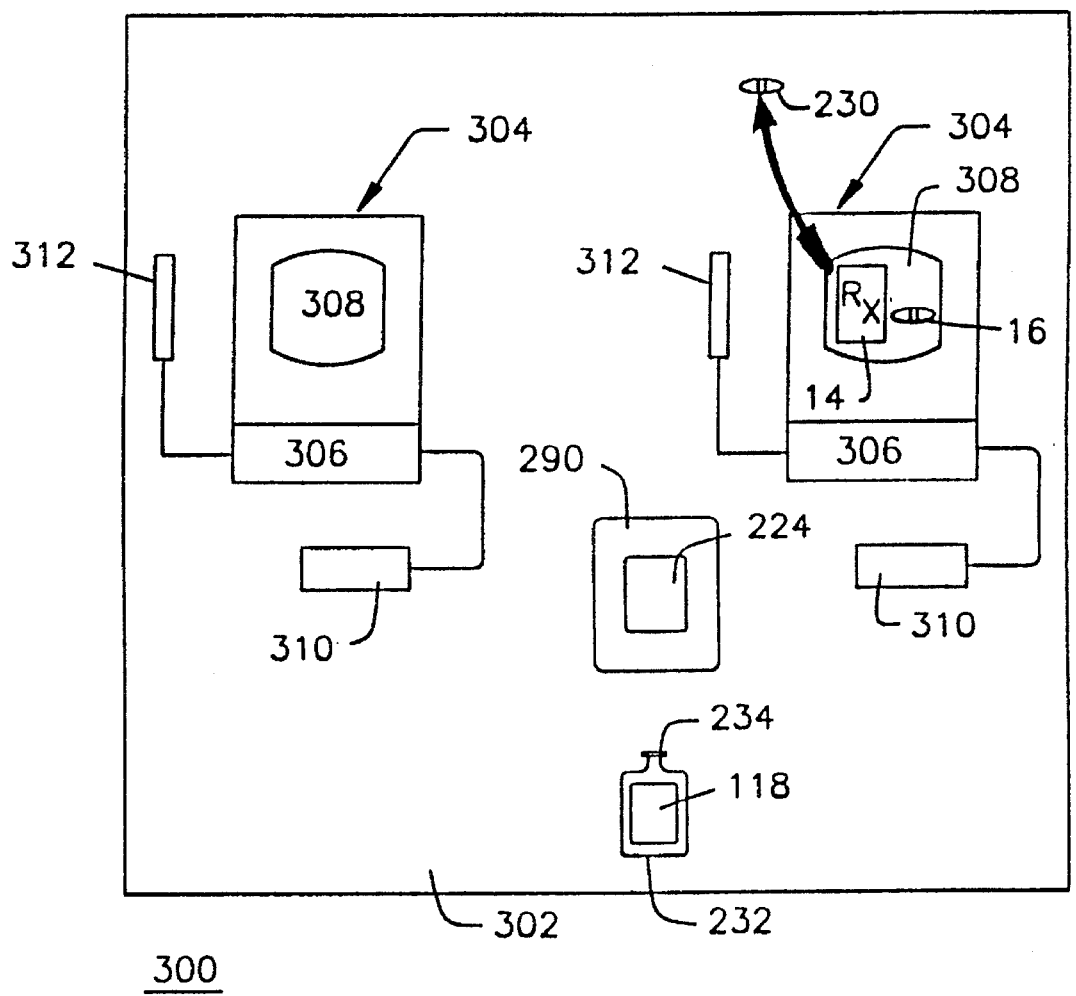
FIG. 6 is a schematic diagram of the checking work station of the pharmacy system of FIG. 1.

The checking work station 300, as depicted in FIG. 6, is used to assist the pharmacist in the final quality-control check of the medical prescription just filled. The checking computer 304 displays both the doctor's original prescription image 14 and an image 16 of the drug product 230 prescribed. This final quality-control check requires that the pharmacist sign off by the use of an electronic bar code wand 310 over the pharmacist's personal bar code 18 that the prescription is filled properly, along with a visual recognition check of the drug 230 prescribed.

Imaging Work Station 100

As shown in FIG. 3, the imaging work station 100 includes an imaging work station area space 102 within the retail pharmacy's processing floor space 22. The work station space 102 has a data-entry host computer 104 with a keyboard 106, a screen 108, and a database storage component 110. There is also a first computer 120 including an image scanner component 140 having an electronic pointer 112, a scanner keyboard 122, a scanner screen 124 for viewing the image 14 of medical prescription 12, a scanner receiver device 126 for scanning the original medical prescription 12, a hand held bar code scanner wand 128 for reading a bar code 18 on the prescription order sheet 222, a scanner database storage 130 for electronically storing the prescription image 14, a bar code printer 132 and an electronic communication means using the RS-232 serial data line 216 for linking of information between the data-entry host computer 104 and the first computer 120 and a label printer 114. The prescription facsimile obtained during scanning is used at a later time by the checking pharmacist to verify the accuracy of the filled medical prescription 12 produced by the transaction data record 220. There may be a plurality of host computers 104 at imaging work station 100 for the inputting of customer data. The data-entry host computer 104 is used for entering customer information supplied by the customer to later generate a transaction data record 220 and a prescription order sheet 222 to be used at the filling work station. The transaction data record 220 and the prescription order sheet data on sheet 222 are stored in the database storage component 110. The transaction data record 220 is transmitted from the database storage 110 to the scanner database storage 130 via the electronic communication means 216. The label printer 114 dispenses the individual prescription labels 118 and order sheets 222 from a dispensing label supply roll 116 from information obtained from the database storage 110 on the medical prescription 12 prescribed. Order sheet 222 includes a vial label 118 having the bar code label 18, bag label(s) 224, and a drug information label(s) 226 attached thereon.

The transaction data record 220 consists of about 20 fields of information, which contain a variety of data input regarding the prescription and filling thereof. The order sheet 222 includes the ℞ labels 118, order information from data record 220, a bar code indicia 18 unique to that order of medical prescription 12 prescribed, a bag label(s) 224 and drug information label(s) 226. The most relevant fields of information on the transaction record are the prescription number, the NDC (National Drug Code) number, and the quantity of drug prescribed. This information allows the medical prescription 12 to be filled at the filling work station area 202. The pharmacy system 10 is designed to have the transaction data record information 220 sent from the computer 104 via the storage database 110 to the filling area's computer 204 via the information sent from the scanner database storage 130. The prescription order sheet 222 is physically moved by the pharmacist/clerk from the printer 114 to the filling work station 200.

The prescription order sheet 222 consists of at least 20 fields of information which contain vital data input for the prescription and filling thereof. The most important and relevant fields of information on the prescription order sheet 222 is that of the name of the patient, prescription number, name of the drug product, name of the doctor, and NDC code number.

Filling Work Station 200

The filling work station 200 includes a filling work station area space 202 adjacent to the imaging work station area 102 within the retail pharmacy's processing floor space 22. The filling work station space 202 has a second computer 204 with a keyboard 206 and a monitoring screen 208; a pointer 212; portable bar code scanner wand 214; a plurality serial data lines 216 for transferring data between computer 204 and drug-dispensing units 240, 250, 260, and 270 and database storage component 110; at least one drug-dispensing unit 240, 250, 260, or 270; and one or more electronic-weighing scales 238, all electronically connected to filling station second computer 204. As shown in FIG. 4, there may be a plurality of second computers 204 for the controlling of dispensing unit 240, 250, 260, or 270.

Other essential equipment includes a packing work station 280 which has an in-process holding component 284 having a plurality of cubby holes 286 with overhead pick lights 288 on each cubby hole 286. The holding component 284 is adjacent to the second computer 204 and is used for the in-process holding of a filled medical prescription before it is checked.

The hard copy of the prescription order sheet 222 is used to initiate the drug fulfillment process when the operator/pharmacist scans the bar code 18 on sheet 222 with the bar code scanner 214 at the filling work station 200. This starts the drug-filling process sequence, as well as the inventory-checking sequence. In response to the scanning of bar code 18 on sheet 222, the second computer 204 retrieves from the scanner database storage 130 the name and location of the drug product 230 to be dispensed and triggers the drug-dispensing unit 240, 250, 260, or 270 to start the filling process of a particular specified medical prescription 12. At the same time, the inventory-checking sequence is also being carried out.

Drug-dispensing unit 250 in this embodiment is a Baker-carousel type and includes a plurality of weighing machines 238, a plurality of counting machines 252 and a plurality of vertical carousels 254 with movable shelves 256. The Baker carousel spins to the appropriate vertical pan 254 selected by second computer 204, and a pick light 258 indicates the position on the shelf 256 to find the drug product 230 for the medical prescription 12 being filled.

Drug-dispensing unit 260 in this embodiment is a Baker-instant access cell type and consists of a plurality of holding cells 262 for holding various drug products 230 having individual drop chutes 264 attached to each holding cell 262. Each holding cell 262 has a number plate 266 attached to the front face of each cell. The Baker-holding cell 262 has an internal counter (not shown) which automatically counts out its drug product 230 contents. The pharmacist places the vial 232 at the mouth of the drop chute 264 of the proper numbered plate 266 and releases the prescribed drug product 230 into vial 232 to fill medical prescription 12 and apply cap 234 to vial 232.

Drug-dispensing unit 270 in this embodiment is a Baker-cassette type and consists of a plurality of holding cassettes 272; and a plurality of cassette counters 274 having individual drop chutes 276 attached to the front of each cassette counter 274 for counting of the dispersed drug product 230. Each holding cassette 272 has a numbered plate 278 attached to the front face of each cassette. The pharmacist is directed by information from database storage 130 and displayed on screen 208 where then the pharmacist goes to the correct Baker cassette with an appropriate vial 232 and chooses the appropriate holding cassette 272, as indicated by the drug location numbered display plate 278, and the pharmacist places a quantity of drug product 230, in the form of pills, tablets, or capsules, into the Baker cassette counter 274. The pharmacist then keys in the quantity required of drug product 230 based upon information from database storage 130. The counter 274 then automatically counts out the prescribed drug product 230 based on that particular information from database storage component 130. The pharmacist then releases the counted drug tablets 230 from chute 276 of cassette counter 274, into a drug vial 232, places a cap 234 on the vial 232, and places the filled medical prescription 12 in an in-process cubby-hole slot 286 of holding component 284.

Drug dispensing unit 240 in this embodiment is a static shelf assembly consisting of a plurality of non-movable shelves 242 having pick-lights 244 attached thereon. Picklight 244 goes ON automatically at the correct static-shelf 242 location from the aforementioned information displayed on screen 208 of second computer 204. The pharmacist is directed, as with the Baker-cassette type, in using the weighing scale 238 to weight-out drug product 230 or using cassette counter 274 for counting of the dispersed drug product 230.

Within the filling work station 200 is the packaging work station 280, which is adjacent to both filling area 202 and checking work station area 302. The packaging work station 280 includes a packaging work station space 282 having on it a package-holding component 284 and packaging tote bag materials 290. The packaging-holding component 284 has a plurality of large cubby-hole slots 286 with pick lights 288 for holding the filled prescription vial(s) 232 and prescription order sheet(s) 222. Also, the packaging work station 280 has its own portable bar code scanner wand 292 to be used for scanning the bar code 18 which in turn triggers the pick light 288 to go ON based upon a family identifier which was contained in the information within the transaction data record 220. The function of packaging work station 280 is to complete, gather, and package one customer's or family's medical prescriptions 12 in the pharmacy system 10 by the filling technician or sales clerk prior to handing the order off to the pharmacist for final checking at checking work station area 302.

The function of filling work station 200 is to count, dispense, and bottle the drug product(s) 230 for every medical prescription 12 that enters the pharmacy system 10. This station's software program 20 stored in the database 130 will accomplish the counting, dispensing, and bottling tasks by controlling all dispensing units 240, 250, 260, and 270. Signals sent to the dispensing units 240, 250, 260, and 270 from database 130 will either count the drug product 230 or will position the equipment for easy drug product 230 selection.

Dispensing units 250 and 260 will provide feedback to database 130 with regard to the remaining inventory. The pharmacy system 10, through databases 110 and 130, provides a current reading of inventory of all drug products 230 as they are used and provides an inventory update to tell the pharmacist when a particular drug product 230 replenishment is needed. As a result of the inventory-tracking ability, the system 10 warns the pharmacist of low-inventory levels and out-of-stock situations of a particular drug product 230. The functions of filling station 200 can only be carried out from the filling station second computer 204 having serial data lines 216 and database storage components 110 and 130.

Checking Work Station 300

The checking work station 300 includes a checking work station area space 302 adjacent to the filling work station area 202 within the retial pharmacy's processing floor space 22. The checking work station space 302 has a third computer 304 with keyboard 306 and screen 308; a bar code scanner wand 310; and a pointer 312, all electronically connected to third computer 304. As shown in FIG. 6, there may be a plurality of third computers 304 for the checking of the fulfilled medical prescription 12 prescribed.

At checking work station 300, the registered pharmacist checks that the proper drug product 230 and quantity for medical prescription 12 has been properly dispensed. Checking is performed by using digitized image 14 of the original written medical prescription 12 and the image of prescribed drug product 16 and comparing them with the actual dispensed drug product 230 being given to the customer. There is a zoom feature on both of the digitized images 14 and 16 being viewed on monitor screen 308, which enables the pharmacist to see the necessary details to make an accurate and proper verification of drug product 230 being dispensed. The zoom feature on the prescription image 14 may also be used to investigate possible alterations to the original prescription 12 being filled. A final QC check requires the pharmacist to sign-off by the use of an electronic bar code wand 310 over the pharmacists' personal bar code 18 that the prescription was filled out properly, along with a visual recognition check of the drug product 230 prescribed from prescription 12. This visual recognition check allows for a first visual comparison between the digitized image 16 of the prescribed drug product 230 and the dispensed drug product 230 in a given drug vial 232, and a second visual comparison between the digitized image 14 of the original medical prescription 12 and the dispensed drug product 230 in a given drug vial 232 before it is given to the customer.

Method of Operation of the Present Invention

In operation, the flow path of the prescription being processed is always from the imaging work station to the filling work station and then to the checking work station. The fulfillment process of pharmacy system 10 starts when the customer presents the doctor's medical prescription 12 to the sales clerk/pharmacist. The information obtained from medical prescription 12 is entered into the database 110 from which it is used to generate parts of the information required on the transaction data record 220 and prescription order sheet 222.

The customer also verbally provides other personal information required by the pharmacy staff to the sales clerk/ pharmacist, who then enters this information in the database 110 by manually inputting it by keyboard 106 of host computer 104. This information is used to generate the remaining parts of the information required for the transaction data record 220 and prescription order sheet 222.

The label printer 114 prints out the prescription order sheet 222 having the vial label 118 with the bar code 18 inscribed thereon and having the label information required by state and federal law, also a bag label 224 and a drug information label 226. Simultaneously, the transaction data record 220 is transmitted via serial data link 216 to the storage database 130. The information for the transaction data record 220 and prescription order sheet 222 is supplied to printer 114 via database 110.

The sales clerk/pharmacist then scans the bar code 18 of vial label 118 of prescription 12 by the hand-held scanner wand 128. The salesclerk/pharmacist then scans the prescription 12 via the scanner receiver 126, thus linking the prescription number contained in the bar code 18 to the image 14 of original medical prescription 12. The image 14 of medical prescription 12 is stored in database 130. The original prescription 12 is filed away by the salesclerk at a later time, as a permanent record for state and federal agencies.

The stored prescription image 14 is used for quality-control checking at checking station 300. Already inputted into the software program 20 and stored in database 130 is a compilation of medical product visual images 16 showing the drug product 230 in the form of a tablet, a pill, a capsule, a caplet, and the like, which is also used for quality-control checking at checking station 300 in the drug-fulfillment process. The prescription order sheet 222 is transferred manually to filling work station 200 for processing.

At the filling work station 200, the pharmacist then scans bar code 18 with scanner wand 214, which initiates the operation of the proper drug-dispensing units 240, 250, 260, and 270. The pharmacist then selects the proper vial 232 based upon the information shown on the display screen 208 of second computer 204, where then the pharmacist applies the label 118 to the properly sized vial 232. The pharmacist then looks at the display screen 208 again to determine the location of the movable shelf 256 for dispensing unit 250 or numbered plate 246, 266, or 278 for dispensing unit 240, 260, or 270.

The bar code 18 on label 118 derived from medical prescription 12 contains the prescription number which serves as an index to transaction data record 220 now stored in storage component 130. The information from storage database 130 is used to determine which drug-dispensing unit 240, 250, 260, or 270 is to be actuated to dispense the correct prescribed drug 230. Thus, when the pharmacist scans label 18, the information required is supplied to second computer 204, which actuates the proper drug-dispensing unit 240, 250, 260, or 270.

If dispensing unit 250 is selected, the dispensing unit 250 will run, such that, the prescribed drug 230 is selected from the correct vertical carousel 254 from movable shelf 256, and then counting machine 252 can be used to count the appropriate quantity of drug 230 to be dispensed. The dispensed drug 230 is received in a holding hopper 236 and weighed by scale 238 for placement in a vial 232 with a cap 234 and a vial label 118.

While the drug-dispensing unit 250 is running, the operator/pharmacist takes the appropriate labeled vial 232 from work space 202 and tabletop 202a and then moves to retrieve the drug product 230 from hopper 236. After retrieving and placing the designated drug 230 into the appropriate vial 232 and capping 234 it, the operator/pharmacist then carries the capped vial 232 and prescription order sheet 222 to the packing station area 282. The operator/pharmacist then scans again, by use of bar scanner 214, the prescription order sheet 222 having the prescription number bar code 18 of the medical prescription prescribed 12. This aforementioned scan of bar code 18 causes a pick light 288 to illuminate, signifying a particular cubby hole 286 of packing work station 280 where the filled prescription has been placed therein by the operator/pharmacist. This process is repeated until all prescriptions from a given order are completed and are placed in this same cubby hole 286.

If dispensing unit 260 is selected, the holding cell 262 automatically counts out the prescribed drug 230. The pharmacist then places the labeled vial 232 at the mouth of drop chute 264 of the proper numbered plate 266 and then releases the prescribed drug product 230 into vial 232 and applies cap 234 to vial 232.

If dispensing unit 270 is selected, the pharmacist then goes to the proper numbered plate 278 of holding cassette 272 and places a quantity of prescribed drug product 230 into counter 274. The counter 274 automatically counts out the prescribed drug product 230 based on information from database storage component 130. The pharmacist then releases the counted drug tablets 230 from chute 276 of cassette counter 274, into a drug vial 232, places a cap 234 on the vial 232, and places the filled medical prescription 12 in an in-process cubby-hole slot 286 of holding component 280.

If dispensing unit 240 is selected, the pharmacist goes to the proper numbered plate 246 of static shelf 242 where a pick light 244 is ON, and picks the proper drug product 230, based upon the information generated on screen 208 of second computer 204. The pharmacist then uses either weighing scale 238 to weigh-out drug product 230 or uses cassette counter 274 for counting of the dispersed drug product 230; where then the pharmacist fills the vial 232 with product 230, places a cap 234, on the vial 232 and places the filled prescription 12 in cubby hole slot 286 of holding component 280. The scanning operation by the pharmacist and the use of the pick light 244 discussed above with regard to dispensing unit 250 are also applicable to the use of dispensing units 260 and 270.

At checking work station 300 the final quality control step of the pharmacy system 10 prescription fulfillment process is completed by the on-duty pharmacist. When the order is complete, this fact is signalled by scanner wand 214 at the filling work station 200 to the on duty pharmacist via display screen 308 of third computer 304. At this time the pharmacist at the checking work station area 302 pulls the prescription order tote 290 from the aforementioned cubby hole 286 and picks one of the prescriptions. The pharmacist scans again the medical prescription bar code 18 from label 118 or order sheet 222 with the scanner wand 310. This scan causes the image 14 of the original medical prescription 12 and the image 16 of the drug product 230 to be displayed on the checking station's 300 terminal screen 308, from these visual queues, the pharmacist verifies that the prescription has been properly filled. This procedure which is done by the pharmacist allows for a first visual comparison between the digitized image 16 of the prescribed drug product 230 and the dispensed drug product 230 in a given drug vial 232, and a second visual comparison between the digitized image 14 of the original medical prescription 12 and the dispensed drug product 230 in a given drug vial 232 before it is given to the customer. When the pharmacist is satisfied that the prescription is correct, he/she scans a personal ID code to signify that he/she has checked the prescription. This process is repeated for all prescriptions in the order. When the order is complete, the pharmacist packages the prescriptions and then puts them into a second prescription-holding component 384, now called a will-call work station 380, having holding slots 386 to be picked up by the customer at a later time. When the customer comes to the pharmacy for pickup, the sales clerk/cashier goes to the proper holding slot 386 of the prescription-holding component 384 and picks the prescription order. The prescription order can be scanned once again with scanner 310 to verify the customer's name and drug(s) 230 prescribed. If correct, the cashier will accept payment and give the prescription order to the customers to complete the medical prescription fulfillment process using the pharmacy system 10.

Advantages of the Present Invention

Accordingly, an advantage of the present invention is that it provides a retail store pharmacy system that automates the medical prescription fulfillment process, including at least of three essential work stations of imaging, filling, and checking, which operate under computer guidance from a common database, with the primary benefits of increased efficiency and lower overall cost.

Another advantage of the present invention is that it provides an imaging work station that is designed to capture an electronic image of the doctor's original prescription to the patient and allows the operator at that work station to set certain prescription processing parameters. This significantly reduces paperwork in the fulfillment process through the use of an imaging system, which maintains the accuracy of the original written prescription.

Another advantage of the present invention is that it provides for a filling work station that controls dispensing equipment, which includes the counting machines and the vertical carousels with movable shelves. This dispensing equipment increases the productivity of the pharmacy by providing access to a broad range of products within a minimum amount of processing floor space of a pharmacy.

Another advantage of the present invention is that it provides for a checking station that is used to assist the pharmacist in the final quality-control checking task, such that the display screen shows both the prescription image and the drug product image, which then requires the pharmacist to sign off that the prescription is filled and labeled properly.

A further advantage of the present invention is that it provides a retail pharmacy system that is unique, efficient, fast, economical, and effective.

A still further advantage of the present invention is that it provides a retail pharmacy system that is easily operated with a minimum of manpower to operate the system.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A pharmacy system for automating the medical prescription fulfillment process for a customer, comprising:
   a) an imaging work station including a host computer for receiving data entry of an original medical prescription for a prescribed drug product and customer information and for producing a prescription transaction data record; a first computer electronically connected to said host computer and including an image scanner for creating a digitized image of said original medical prescription; a first printer for printing a prescription label for applying to a drug vial for receiving a dispensed drug product; a second printer for printing a bar code label for applying to said drug vial; and means for communicating said prescription transaction data record from said host computer to said first computer;
   b) a filling work station having a second computer electronically connected to said first computer at said imaging work station and further including dispensing means for counting, dispensing, and packaging of said dispensed drug product into said drug vial for the customer, and said second computer for controlling said dispensing means; and
   c) a checking work station having a third computer electronically connected to said second computer at said filling work station and including a scanner for scanning said bar code label on said drug vial, and a display for displaying said digitized image of said original medical prescription, and for displaying a digitized image of said prescribed drug product to allow a first visual comparison between said digitized image of said prescribed drug product and said dispensed drug product in said drug vial, and a second visual comparison between said digitized image of said original medical prescription and said dispensed drug product in said drug vial before it is given to the customer.

2. A pharmacy system in accordance with claim 1, further including a packaging work station having a holding station which includes a plurality of holding compartments for packaging of said dispensed drug product for said customer's use.

3. A pharmacy system in accordance with claim 2, wherein said checking work station further includes a will-call work station having a plurality of compartments for holding in-process prescriptions and filled prescriptions until they are taken from said checking work station to the customer.

4. A pharmacy system in accordance with claim 1, wherein said imaging work station further includes a monitor for displaying said transaction data record and database storage means for storing said transaction data record.

5. A pharmacy system in accordance with claim 1, wherein said imaging work station further includes a portable bar code scanner for scanning said bar code label.

6. A pharmacy system in accordance with claim 1, wherein said image scanner includes a keyboard, a scanner screen, a scanner receiver, and database storage means for retention of said digitized image of said original medical prescription.

7. A pharmacy system in accordance with claim 1, wherein said filling work station further includes a portable bar code scanner for scanning said bar code label and actuating a preselected dispensing unit in response thereto.

8. A pharmacy system in accordance with claim 1, wherein said dispensing means includes a plurality of dispensing carousels having a plurality of movable shelves for holding bottles of drug products within said dispensing carousels, a plurality of counting devices electronically connected to said dispensing carousels, and a plurality of weighing scales electronically connected to said dispensing carousels.

9. A pharmacy system in accordance with claim 1, wherein said dispensing means includes a plurality of dispenser-holding cells each having an internal counter and drop chutes attached thereto for automatically counting and dispensing of said drug product into said drug vial.

10. A pharmacy system in accordance with claim 1, wherein said dispensing means includes a plurality of dispenser-holding cassettes each having a plurality of cassette counters with drop chutes attached thereto for automatically counting and dispensing of said drug product into said drug vial.

11. A pharmacy system for automating the medical prescription fulfillment process for a customer, comprising the steps of:
   a) at an imaging work station having a host computer, entering into said host computer an original medical prescription for a prescribed drug product and customer information and producing a prescription transaction data record; creating a digitized image of said original medical prescription using an image scanner; printing a prescription label for applying to a drug vial for receiving a dispensed drug product; and printing a bar code label for applying to said drug vial;

b) at a filling work station located adjacent to said imaging work station, counting, dispensing and packaging of said dispensed drug product into said drug vial for the customer; and c) at a checking work station located adjacent to said filling work station, scanning said bar code label on said drug vial, and displaying said digitized image of said original medical prescription, and displaying a digitized image of said prescribed drug product to allow a first visual comparison between said digitized image of said prescribed drug product and said dispensed drug product in said drug vial, and a second visual comparison between said digitized image of said original medical prescription and said dispensed drug product in said drug vial before it is given to the customer.

12. A pharmacy system in accordance with claim 11, further including the step of printing bag labels and drug information labels.

13. A pharmacy system in accordance with claim 11, further including the steps of moving, labeling, bagging, and holding said prescribed drug product at a packaging work station.

* * * * *